United States Patent [19]

Takaya et al.

[11] Patent Number: 4,463,002
[45] Date of Patent: Jul. 31, 1984

[54] SYN-ISOMERS OF 7-SUBSTITUTED-3-CEPHEM-4-CARBOXYLIC ACID ESTERS

[75] Inventors: Takao Takaya, Kawanishi; Hisashi Takasugi, Suminoe; Kiyoshi Tsuji, Kishiwada; Toshiyuki Chiba, Higashinari, all of Japan

[73] Assignee: Fujisawa Pharmaceutical Co., Ltd., Osaka, Japan

[21] Appl. No.: 378,334

[22] Filed: May 14, 1982

Related U.S. Application Data

[60] Continuation-in-part of Ser. No. 302,668, Sep. 15, 1981, Pat. No. 4,427,674, which is a division of Ser. No. 886,340, Mar. 14, 1978.

[30] Foreign Application Priority Data

May 21, 1981 [JP] Japan .................. 56-77447

[51] Int. Cl.³ .................. A61K 31/545; C07D 501/20
[52] U.S. Cl. .................. 424/246; 544/22
[58] Field of Search .................. 544/22; 424/246

[56] References Cited

U.S. PATENT DOCUMENTS 4,278,793  7/1981  Dürckheimer et al. .............. 544/22
4,298,529  11/1981  Ueda et al. .............. 544/22
4,299,829  11/1981  Kamiya et al. .............. 544/22
4,368,325  1/1983  Ueda et al. .............. 544/22

FOREIGN PATENT DOCUMENTS 8343  3/1980  European Pat. Off. .
2810922  9/1978  Fed. Rep. of Germany .

Primary Examiner—Paul M. Coughlan, Jr.
Attorney, Agent, or Firm—Oblon, Fisher, Spivak, McClelland & Maier

[57] ABSTRACT

This invention relates to novel cephem compounds of high antimicrobial activity comprising the syn-isomers of 7-substituted-3-cephem-4-carboxylic acid esters of the formula:

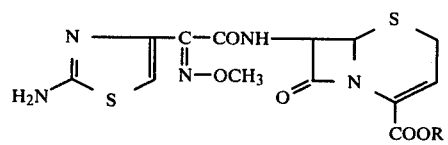

wherein R is lower alkanoyloxy $(C_2-C_6)$alkyl, isobutyryloxymethyl, 2-ethylbutyryloxymethyl or 3,3-dimethylbutyryloxymethyl, or salts thereof.

5 Claims, No Drawings

SYN-ISOMERS OF 7-SUBSTITUTED-3-CEPHEM-4-CARBOXYLIC ACID ESTERS

This application is a continuation-in-part of application Ser. No. 302,668, filed Sept. 15, 1981, now U.S. Pat. No. 4,427,674, which in turn is a division of application Ser. No. 886,340, filed Mar. 14, 1978.

The present invention relates to novel syn-isomers of 7-substituted-3-cephem-4-carboxylic acid esters and pharmaceutically acceptable salts thereof.

More particularly, it relates to novel syn-isomers of 7-substituted-3-cephem-4-carboxylic acid esters and pharmaceutically acceptable salts thereof, which have antimicrobial activity, to process for the production of the same, to a pharmaceutical composition comprising the same, and to a method of using the same therapeutically in the treatment of infectious diseases in human being or animals.

Accordingly, one object of the present invention is to provide the novel syn-isomers of 7-substituted-3-cephem-4-carboxylic acid esters and pharmaceutically acceptable salts thereof, which are highly active against a number of pathogenic microorganisms and are useful as antimicrobial agents, especially for oral administration.

Another object of the present invention is to provide a process for the production of novel syn-isomers of 7-substituted-3-cephem-4-carboxylic acid esters and salts thereof.

A further object of the present invention is to provide a pharmaceutical composition comprising, as active ingredients, said syn-isomers of 7-substituted-3-cephem-4-carboxylic acid esters and pharmaceutically acceptable salts thereof.

Still further object of the present invention is to provide a method of using said syn-isomers of 7-substituted-3-cephem-4-carboxylic acid esters and pharmaceutically acceptable salts thereof in the treatment of infectious diseases by pathogenic microorganisms in human being or animals.

The syn-isomers of 7-substituted-3-cephem-4-carboxylic acid esters according to this invention are novel and can be represented by the following general formula:

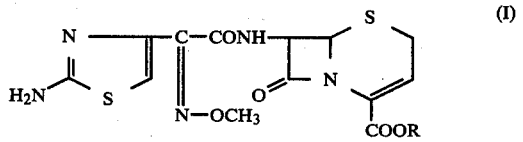

wherein R is lower alkanoyloxy($C_2$–$C_6$)alkyl, isobutyryloxymethyl, 2-ethylbutyryloxymethyl or 3,3-dimethylbutyryloxymethyl.

Suitable salts of the object compound (I) may include any pharmaceutically acceptable salts such as inorganic acid addition salts (e.g. hydrochloride, hydrobromide, sulfate, phosphate, etc.), organic carboxylic acid or sulfonic acid addition salts (e.g. formate, acetate, trifluoroacetate, maleate, tartarate, methanesulfonate, benzenesulfonate, p-toluenesulfonate, etc.), acidic amino acid salts (e.g. aspartic acid, glutamic acid, etc.), or the like.

The object compound (I) or salts thereof of this invention can be produced by the process illustrated below.

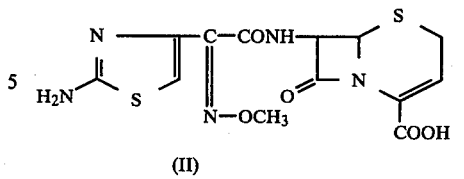

or salts thereof

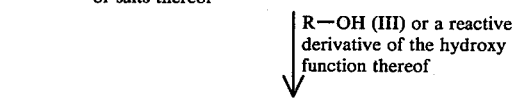

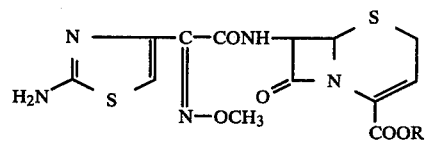

or salts thereof wherein R is as defined above.

In the above description of the present specification, suitable examples and illustration of the definition to be included within the scope thereof are explained in details as follows.

Suitable lower alkanoyloxy($C_2$–$C_6$)alkyl group for R may be, for example, 1 (or 2)-acetoxyethyl, 1 (or 2 or 3)-acetoxypropyl, 1 (or 2 or 3 or 4)-acetoxybutyl, 1 (or 2)-propionyloxyethyl, 1 (or 2 or 3)-propionyloxypropyl, 1 (or 2)-butyryloxyethyl, 1 (or 2)-isobutyryloxyethyl, 1 (or 2)-pivaloyloxyethyl, 1 (or 2)-pentanoyloxyethyl, 1 (or 2)-hexanoyloxyethyl or the like.

The process for production of the compound (I) or salts thereof will be explained in detail as follows.

The compound (I) or salts thereof is produced by reacting compound (II) or salts thereof with an alcohol compound (III) or a reactive derivative of the hydroxy function thereof.

The salts of the starting compound (II) used in this invention are exemplified by the salts with metals, e.g. sodium, potassium, calcium, magnesium, etc., and salts with organic bases, e.g. ammonium, triethylamine, pyridine, etc., as well as the salts corresponding to those mentioned for the compound (I).

The reactive derivative of the hydroxy function of the alcohol compound (III) may, for example, be the compound (III) whose hydroxy group has been substituted by an acid residue such as halogen, e.g. chlorine, bromine, iodine, etc., and the like.

In the present invention, in case that the alcohol compound (III) is used in the form of the reactive derivative of its hydroxy function, the reaction is conducted in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate, (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoate (e.g. sodium acetate, etc.), trialkylamine (e.g. triethylamine, etc.), pyridines (e.g. pyridine, lutidine, picoline, etc.), quinoline and the like, and in case that the reactive derivative of the hydroxy function of the compound (III) is a halide other than the iodide, the reaction is often conducted in the presence of a metal iodide such as sodium iodide.

Further, in case that the alcohol compound (III) is used in a free form in this reaction, the reaction is preferably conducted in the presence of a condensing agent which is generally employed for esterification.

This reaction is usually conducted in a solvent which does not adversely influence the reaction such as acetone, dioxane, acetonitrile, chloroform, benzene, methylene chloride, ethylene chloride, tetrahydrofuran, ethyl acetate, dimethylsulfoxide, N,N-dimethylformamide, pyridine, hexamethylphosphoramide, etc. or a mixture thereof.

The reaction temperature is not critical, and the reaction is in many cases conducted under cooling, at room temperature or under heating.

The object compound (I) thus obtained may be converted to pharmaceutically acceptable salts in a conventional manner.

The object compound (I) and pharmaceutically acceptable salts thereof of this invention possess high antimicrobial activity and are useful in the prophylaxis and treatment of infectious diseases caused by pathogenic microorganisms, especially, it can also be used as an oral preparation.

For therapeutic administration, the object compound (I) and the pharmaceutically acceptable salts thereof of the present invention are used in the form of conventional pharmaceutical preparation which contains said compounds, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound (I) of the present invention may be used in treating diseases infected by pathogenic microorganisms.

The following examples are given for the purpose of illustrating the present invention.

EXAMPLE 1

To a solution of sodium 7-[2-(2-aminothiazol-4-yl)-2-methoxyiminoacetamido]-3-cephem-4-carboxylate (syn-isomer, 4.0 g) in dimethylsulfoxide (40 ml) were added 1-bromoethyl propionate (1.8 g) and sodium iodide (0.18 g), and the mixture was stirred at room temperature for 30 minutes. The reaction mixture was poured into a mixture of cold water and ethyl acetate, and the organic layer was separated. The remaining aqueous layer was extracted with ethyl acetate. The extract and the organic layer were combined, washed with water and dried over magnesium sulfate. The solvent was then distilled off and the residue was subjected to column chromatography using silica gel (50 g), elution being carried out with a mixture of benzene and ethyl acetate (3:2, v/v). The fractions containing the desired product were combined and the solvent was distilled off to give 1-propionyloxyethyl 7-[2-(2-aminothiazol-4-yl)-2-methoxyiminoacetamido]-3-cephem-4-carboxylate (syn isomer, 0.83 g), mp 113°–116° C. (decompn.).

IR (Nujol): 3300, 1775, 1672 cm$^{-1}$.

NMR $\delta$ppm (DMSO-$d_6$): 1.06 (3H, t, J=8 Hz), 1.53 (3H, d, J=5 Hz), 2.45 (2H, q, J=8 Hz), 3.75 (2H, broad s), 4.00 (3H, s), 5.32 (1H, d, J=5 Hz), 6.06 (1H, dd, J=5,8 Hz), 6.83 (1H, t, J=4 Hz), 6.98 (1H, s), 7.15 (1H, q, J=5.5 Hz), 7.46 (2H, s), 9.96 (1H, d, J=8 Hz).

EXAMPLE 2

In the same manner as Example 1, sodium 7-[2-(2-aminothiazol-4-yl)-2-methoxyiminoacetamido]-3-cephem-4-carboxylate (syn-isomer) was reacted with 1-bromopropyl propionate in the presence of sodium iodide to give 1-propionyloxypropyl 7-[2-(2-aminothiazol-4-yl)-2-methoxyiminoacetamido]-3-cephem-4-carboxylate (syn-isomer), mp 100°–108° C. (decompn.).

IR (Nujol): 3420, 3310, 1775, 1735, 1675, 1630 cm$^{-1}$.

NMR $\delta$ppm (DMSO-$d_6$): 0.7–1.2 (6H, m), 1.75 (2H, q, J=6.5 Hz), 2.37 (2H, q, J=7.5 Hz), 3.6 (2H, m), 3.83 (3H, s), 5.12 (1H, d, J=5 Hz), 5.85 (1H, dd, J=5.7 Hz), 6.4–7.0 (2H, m), 6.72 (1H, s), 7.22 (2H, broad s).

EXAMPLE 3

In the same manner as Example 1, sodium 7-[2-(2-aminothiazol-4-yl)-2-methoxyiminoacetamido]-3-cephem. 4-carboxylate (syn-isomer) was reacted with 1-bromopropyl acetate in the presence of sodium iodide to give 1-acetoxypropyl 7-[2-(2-aminothiazol-4-yl)-2-methoxyiminoacetamido]-3-cephem-4-carboxylate (syn-isomer), mp 110°–116° C. (decompn.).

IR (Nujol): 3400, 3300, 1770, 1750, 1670, 1620 cm$^{-1}$.

NMR $\delta$ppm (DMSO-$d_6$+$D_2O$): 0.97 (3H, t, J=7 Hz), 1.76 (2H, m), 2.07 (3H, s), 3.63 (2H, broad s), 3.85 (3H, s), 5.15 (1H, d, J=4.5 Hz), 5.88 (1H, d, J=4.5 Hz), 6.4–7.0 (2H, m), 6.73 (1H, s).

EXAMPLE 4

In the same manner as Example 1, sodium 7-[2-(2-aminothiazol-4-yl)-2-methoxyiminoacetamido]-3-cephem-4-carboxylate (syn-isomer) was reacted with 1-bromoethyl isobutyrate in the presence of sodium iodide to give 1-isobutyryloxyethyl 7-[2-(2-aminothiazol-4-yl)-2-methoxyiminoacetamido]-3-cephem-4-carboxylate (syn-isomer), mp 120°–125° C. (decompn.).

IR (Nujol): 3300, 1772, 1740, 1673 cm$^{-1}$.

NMR $\delta$ppm (DMSO-$d_6$): 1.10 (6H, d, J=6.5 Hz), 1.45 (3H, d, J=5 Hz), 2.3–2.7 (1H, m), 3.6 (2H, m), 3.83 (3H, s), 5.12 (1H, d, J=5 Hz), 5.85 (1H, dd, J=5,8 Hz), 6.6 (1H, broad t, J=4 Hz), 6.70 (1H, s), 6.88 (1H, q, J=5 Hz), 7.16 (2H, s), 9.56 (1H, d, J=8 Hz).

EXAMPLE 5

In the same manner as Example 1, sodium 7-[2-(2-aminothiazol-4-yl)-2-methoxyiminoacetamido]-3-cephem-4-carboxylate (syn isomer) was reacted with 1-bromoethyl acetate in the presence of sodium iodide to give 1-acetoxyethyl 7-[2-(2-aminothiazol-4-yl)-2- methoxyiminoacetamido]-3-cephem-4-carboxylate (syn-isomer), mp 100°–103° C. (decompn.).

IR (Nujol): 3310, 1775, 1730, 1675 cm$^{-1}$.

NMR δppm (DMSO-d$_6$): 1.43 (3H, d, J=5.5 Hz), 2.00 (3H, s), 3.39 (2H, broad s), 3.76 (3H, s), 5.07 (1H, d, J=4.5 Hz), 5.80 (1H, dd, J=4.5, 8 Hz), 6.53 (1H, t, J=4 Hz), 6.66 (1H, s), 6.81 (1H, q, J=5.5 Hz), 7.13 (2H, s), 9.50 (1H, d, J=8 Hz).

EXAMPLE 6

In the same manner as Example 1, sodium 7-[2-(2-aminothiazol-4-yl)-2-methoxyiminoacetamido]-3-cephem-4-carboxylate (syn-isomer) was reacted with 1-bromobutyl acetate in the presence of sodium iodide to give 1-acetoxybutyl 7-[2-(2-aminothiazol-4-yl)-2-methoxyiminoacetamido]-3-cephem-4-carboxylate (syn-isomer), mp 100°–105° C. (decompn.).

IR (Nujol): 3300, 1765, 1670 cm$^{-1}$.

NMR δppm (DMSO-d$_6$): 0.90 (3H, t, J=6 Hz), 1.20–1.95 (4H, m), 2.03 (3H, s), 3.6 (2H, m), 3.83 (3H, s), 5.15 (1H, d, J=4.5 Hz), 5.88 (1H, dd, J=4.5, 8 Hz), 6.63 (1H, t, J=4 Hz), 6.76 (1H, s), 6.88 (1H, t, J=5.5 Hz), 7.20 (2H, s), 9.66 (1H, d, J=8 Hz).

EXAMPLE 7

In the same manner as Example 1, sodium 7-[2-(2-aminothiazol-4-yl)-2-methoxyiminoacetamido]-3-cephem-4-carboxylate (syn-isomer) was reacted with 1-iodoethyl pivalate in the presence of sodium iodide to give 1-pivaloyloxyethyl 7-[2-(2-aminothiazol-4-yl)-2-methoxyiminoacetamido]-3-cephem-4-carboxylate (syn-isomer), mp 110°–115° C. (decompn.).

IR (Nujol): 3370, 1780, 1750, 1680 cm$^{-1}$.

NMR δppm (DMSO-d$_6$): 1.13 (9H, s), 1.45 (3H, d, J=5 Hz), 3.48, 3.75 (2H, ABq, J=10 Hz), 3.83 (3H, s), 5.11 (1H, d, J=4.5 Hz), 5.84 (1H, dd, J=4.5, 8 Hz), 6.58 (1H, broad t, J=4 Hz), 6.71 (1H, s), 6.84 (1H, q, J=5 Hz), 7.16 (2H, s), 9.66 (1H, d, J=8 Hz).

EXAMPLE 8

In a mixture of dry dimethylsulfoxide (150 ml) and dry dimethylformamide (50 ml) was dissolved 7-[2-(2-aminothiazol-4-yl)-2-methoxyiminoacetamido]-3-cephem-4-carboxylic acid (syn-isomer, 10.0 g), and triethylamine (2.6 g) was added dropwise thereto under stirring at 7° C. over 5 minutes. To this solution was added dropwise iodomethyl 3,3-dimethylbutyrate (6.6 g) under stirring at 6°–7° C. over 10 minutes, and the mixture was stirred at 3°–7° C. for an hour. The reaction mixture was poured into ice-water (900 ml), and the collected precipitate by filtration was dissolved in ethyl acetate (150 ml). On the other hand, the filtrate was adjusted to pH 8.0 by 5% aqueous sodium bicarbonate and extracted with ethyl acetate (200 ml×1, 100 ml×1). The extract and the above ethyl acetate solution are combined, washed with 5% aqueous sodium bicarbonate (50 ml) and saturated aqueous sodium chloride (100 ml×2) in that order, and dried over magnesium sulfate. The solvent was then distilled off and the resultant brown residue (14.9 g) was subjected to column chromatography using silica gel (145 g), elution being carried out with a mixture of methanol and chloroform (5:95, v/v) and then with a mixture of acetone and chloroform (3:7, v/v). The fractions (400 ml) containing the desired product were combined and the solvent was distilled off under reduced pressure. The resultant foamy substance (6.7 g) was treated with a mixture of chloroform (50 ml) and diethyl ether (150 ml) to give a light brown powder (4.5 g). This powder was column-chromatographed on silica gel (100 g) and eluted with a mixture of acetone and chloroform (1:3, v/v). The fractions (740 ml) containing the desired product were combined and the solvent was then distilled off under reduced pressure. The resultant foamy product (4.0 g) was treated with diisopropyl ether (200 ml) to obtain a powdery product, which was dried under reduced pressure for 8 hours to give a pale yellow powder of 3,3-dimethylbutyryloxymethyl 7-[2-(2-aminothiazol-4-yl)-2-methoxyiminoacetamido]-3-cephem-4-carboxylate (syn-isomer, 3.8 g), mp 103°–108° C. (decompn.).

IR (Nujol): 3410, 3305, 3200, 1770, 1750, 1670, 1620 cm$^{-1}$.

NMR δppm (CDCl$_3$): 1.03 (9H, s), 2.26 (2H, s), 3.50–3.66 (2H, m), 4.03 (3H, s), 5.07 (1H, d, J=5.0 Hz), 5.79 (2H, s), 5.86 (2H, s), 6.07 (1H, ABq, J=9.0, 5.0 Hz), 6.56–6.66 (1H, m), 6.69 (1H, s), 8.00 (1H, d, J=9.0 Hz).

EXAMPLE 9

In the same manner as Example 8, 7-[2-(2-aminothiazol-4-yl)-2-methoxyiminoacetamido]-3-cephem-4-carboxylic acid (syn-isomer) was reacted with iodomethyl isobutyrate in the presence of triethylamine to give isobutyryloxymethyl 7-[2-(2-aminothiazol-4-yl)-2-methoxyiminoacetamido]-3-cephem-4-carboxylate (syn-isomer), mp 95°–100° C. (decompn.).

IR (Nujol): 3400, 3300, 1770, 1750, 1645, 1630 cm$^{-1}$.

NMR δppm (CDCl$_3$): 1.26 (6H, d, J=7.0 Hz), 2.60 (1H, q, J=7.0 Hz), 3.50–3.67 (2H, m), 4.07 (3H, s), 4.14 (1H, d, J=5.0 Hz), 5.92 (2H, s), 6.00 (2H, s), 6.15 (1H, ABq, J=9.0, 5.0 Hz), 6.59–6.69 (1H, m), 6.76 (1H, s), 8.07 (1H, d, J=9.0 Hz).

EXAMPLE 10

In the same manner as Example 8, 7-[2-(2-aminothiazol-4-yl)-2-methoxyiminoacetamido]-3-cephem-4-carboxylic acid (syn-isomer) was reacted with iodomethyl 2-ethylbutyrate in the presence of triethylamine to give 2-ethylbutyryloxymethyl 7-[2-(2-aminothiazol-4-yl)-2-methoxyiminoacetamido]-3-cephem-4-carboxylate (syn-isomer).

IR (Nujol): 3400, 3300, 3100, 1770, 1745, 1650, 1620 cm$^{-1}$.

NMR δppm (CDCl$_3$): 1.13 (6H, t, J=7.0 Hz), 1.63 (4H, q, J=7.0 Hz), 2.33 (1H, m), 3.50–3.66 (2H, m), 4.10 (3H, s), 5.13 (1H, d, J=5.0 Hz), 5.63 (2H, s), 5.97 (2H, s), 6.15 (1H, ABq, J=9.0, 5.0 Hz), 6.56–6.76 (1H, m), 6.83 (1H, s), 7.89 (1H, d, J=9.0 Hz).

EXAMPLE 11

To a solution of 7-[2-(2-aminothiazol-4-yl)-2-methoxyiminoacetamido]-3-cephem-4-carboxylic acid (syn-isomer, 100 g) in dimethylsulfoxide (650 ml) was added potassium carbonate (21.6 g). Thereto was added 1-chloroethyl propionate (42.8 g) at 40° C. and the mixture was stirred at the same temperature for 2 hours. The reaction mixture was poured into a mixture of ice-water (3 l) and ethyl acetate (2 l), and the separated organic layer was washed in turn with 5% aqueous sodium bicarbonate (300 ml×2), water (300 ml) and an aqueous sodium chloride, followed by drying over magnesium sulfate. After treating with activated charcoal, the solvent was removed by evaporation, and the residue was pulverized with diisopropyl ether to give 1-propionyloxyethyl 7-[2-(2-aminothiazol-4-yl)-2-methoxyiminoacetamido]-3-cephem-4-carboxylate (syn-isomer, 80 g).

IR (Nujol): 3300, 1775, 1672 cm$^{-1}$.

EXAMPLE 12

To a solution of 1-propionyloxyethyl 7-[2-(2-aminothiazol-4-yl)-2-methoxyiminoacetamido]-3-cephem-4-carboxylate (syn-isomer, 7.8 g) was bubbled hydrogen chloride for three minutes, and the solution was stirred for 10 minutes in a stream of nitrogen gas. The precipitates were collected by decantation and pulverized with diethyl ether to give hydrochloride of 1-propionyloxyethyl 7-[2-(2-aminothiazol-4-yl)-2methoxyiminoacetamido]-3-cephem-4-carboxylate (syn-isomer, 7.6 g).

IR (Nujol): 3260, 1780, 1715, 1655, 1620 cm$^{-1}$.

NMR δppm (DMSO-d$_6$): 1.00 (3H, t, J=7.0 Hz), 1.47 (3H, d, J=5.0 Hz), 2.34 (2H, q, J=7.0 Hz), 3.67 (2H, m), 3.90 (3H, s), 5.12 (1H, d, J=5.0 Hz), 5.81 (1H, m), 6.62 (1H, m), 6.85 (1H, m), 6.92 (1H, s), 8.08 (2H, broad s), 9.77 (1H, d, J=8.0 Hz).

EXAMPLE 13

To a solution of 1-propionyloxyethyl 7-[2-(2-aminothiazol-4-yl)-2-methoxyiminoacetamido]-3-cephem-4-carboxylate (syn-isomer, 10 g) in ethyl acetate (100 ml) was added conc. hydrochloric acid (2.2 ml) at 10° C., and the mixture was stirred at the same temperature for 30 minutes. The precipitated materials were collected by filtration and washed with ethyl acetate to give hydrochloride of 1-propionyloxyethyl 7-[2-(2-aminothiazol-4-yl)-2-methoxyiminoacetamido]-3-cephem-4-carboxylate (syn-isomer, 9.2 g).

IR (Nujol): 3260, 1780, 1715, 1655, 1620 cm$^{-1}$.

What we claim is:

1. Syn-Isomers of 7-substituted-3-cephem-4-carboxylic acid esters of the formula:

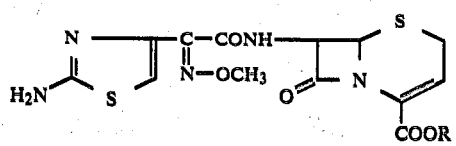

wherein R is 2-ethylbutyryloxymethyl or 3,3-dimethylbutyryloxymethyl, or salts thereof.

2. A compound of claim 1, which is 2-ethylbutyryloxymethyl 7-[2-(2-aminothiazol-4-yl)-2-methoxyiminoacetamido]-3-cephem-4-carboxylate (syn-isomer).

3. A compound of claim 1, which is 3,3-dimethylbutyryloxymethyl 7-[2-(2-aminothiazol-4-yl)-2-methoxyiminoacetamido]-3-cephem-4-carboxylate (syn-isomer).

4. A pharmaceutical composition which comprises, as active ingredients, an effective amount of the compound claimed in claim 1, in admixture with pharmaceutically acceptable carriers.

5. A method for treating infectious diseases caused by pathogenic microorganisms, which comprises administering an effective amount of the compound claimed in claim 1 to infected human being or animals.